United States Patent
Itsuji

(10) Patent No.: US 7,633,299 B2
(45) Date of Patent: Dec. 15, 2009

(54) INSPECTION APPARATUS USING TERAHERTZ WAVE

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 523 days.

(21) Appl. No.: 10/587,262

(22) PCT Filed: Mar. 22, 2006

(86) PCT No.: PCT/JP2006/306393

§ 371 (c)(1),
(2), (4) Date: Jul. 26, 2006

(87) PCT Pub. No.: WO2006/101252

PCT Pub. Date: Sep. 28, 2006

(65) Prior Publication Data
US 2009/0009190 A1    Jan. 8, 2009

(30) Foreign Application Priority Data
Mar. 24, 2005    (JP) .............................. 2005-087326

(51) Int. Cl.
*G01R 27/04* (2006.01)
*G01R 27/32* (2006.01)
(52) U.S. Cl. ...................... 324/639; 324/637
(58) Field of Classification Search ................. 324/639, 324/637
See application file for complete search history.

(56) References Cited

U.S. PATENT DOCUMENTS

| 5,623,145 | A  | 4/1997  | Nuss        |
|-----------|----|---------|-------------|
| 5,977,780 | A  | 11/1999 | Herrmann    |
| 6,448,553 | B1 | 9/2002  | Itsuji et al. |
| 6,835,925 | B2 | 12/2004 | Itsuji et al. |
| 7,248,995 | B2 | 7/2007  | Itsuji et al. |
| 2003/0122628 | A1* | 7/2003  | Aikawa et al. .......... 331/107 G |
| 2004/0227088 | A1  | 11/2004 | Trotz et al. |
| 2005/0201896 | A1* | 9/2005  | Peck .......................... 422/68.1 |
| 2006/0061510 | A1  | 3/2006  | Itsuji      |

(Continued)

FOREIGN PATENT DOCUMENTS

JP    6-18421 A    1/1994

(Continued)

OTHER PUBLICATIONS

M. Nagel, et al., "Integrated THz Technology for Label-Free Genetic Diagnostics" Applied Physics Letters, vol. 80, No. 1, Jan. 7, 2002, pp. 154 to 156.

(Continued)

*Primary Examiner*—Amy He
(74) *Attorney, Agent, or Firm*—Fitzpatrick, Cella, Harper & Scinto

(57) ABSTRACT

An inspection apparatus has a configuration which can suppress attenuation of an electromagnetic wave caused by an environment surrounding the inspection apparatus and can readily prevent an unwanted substance from being contaminated into a propagation path of the electromagnetic wave. The inspection apparatus includes a substrate having therein a structure for holding an inspected object, an electromagnetic wave transmitting portion having an antenna structure and an electromagnetic wave receiving portion having an antenna structure. The electromagnetic wave transmitting portion and the electromagnetic wave receiving portion are disposed in contact with the substrate.

12 Claims, 7 Drawing Sheets

U.S. PATENT DOCUMENTS

| | | | | |
|---|---|---|---|---|
| 2006/0085160 | A1* | 4/2006 | Ouchi | 702/150 |
| 2006/0188398 | A1* | 8/2006 | Yano et al. | 422/82.01 |
| 2007/0030115 | A1 | 2/2007 | Itsuji et al. | |
| 2007/0235658 | A1* | 10/2007 | Zimdars et al. | 250/390.07 |
| 2007/0235718 | A1 | 10/2007 | Kasai et al. | |

FOREIGN PATENT DOCUMENTS

| | | |
|---|---|---|
| JP | 8-320254 A | 12/1996 |
| JP | 2002-257629 A | 9/2002 |
| WO | 2005/001505 A1 | 1/2005 |
| WO | 2006/011668 A1 | 2/2006 |

OTHER PUBLICATIONS

PCT International Search Report and Written Opinion in International Application No. PCT/JP2006/306393; Mailing Date Jul. 11, 2006.

U.S. Appl. No. 12/023,863, filed Jan. 31, 2008, Applicant: Takeaki Itsuji.

U.S. Appl. No. 12/037,780, filed Feb. 26, 2008, Applicant: Takeaki Itsuji.

Official Action in European Application No. 06730341.2; Mailing Date Mar. 18, 2008.

* cited by examiner

INSPECTION APPARATUS USING TERAHERTZ WAVE

TECHNICAL FIELD

The present invention relates to an inspection apparatus performing analysis of physical properties or the like of an object (hereinafter sometimes referred to as "inspected object") by use of an electromagnetic wave, and more particularly to an inspection apparatus which is suitable when an electromagnetic wave of a range of millimeter-wave to terahertz-wave is used. Also, the present invention relates to a technique of performing analysis, identification or the like of an inspected object based on physical property information of the inspected object.

BACKGROUND ART

In recent years, there has been developed a nondestructive inspection technique using a high-frequency electromagnetic wave (hereinafter generally referred to as "terahertz wave" for convenience of description) of a range from millimeter-wave to terahertz-wave (30 GHz-30 THz). In the frequency range of the terahertz wave, there exist absorption lines of a variety of substances including biomolecules. Accordingly, as application fields of electromagnetic waves of this frequency band, there are expected a technique of performing imaging by means of a safer fluoroscopic apparatus as a substitute for X-ray, a spectral technique of determining an absorption spectrum or complex dielectric constant of the interior of a substance to examine a bonding state, a technique of analyzing biomolecules, a technique of estimating carrier concentration or mobility, and so on.

As an object inspection apparatus using a terahertz wave, there has been disclosed, as shown in FIG. 9, an apparatus for irradiating an object 4 with a terahertz wave propagating through a space and identifying the constituent material of the object 4 based on a change in the characteristics of the wave transmitted through the object 4 (Japanese Patent Application Laid-Open Nos. H08-320254 and 2002-257629). At this time, the object 4 can be two-dimensionally scanned to provide a transmission image of the interior of the object 4.

Further, although not using the frequency range of the terahertz wave, there has been disclosed a technique relating to an inspection apparatus obtained by integrating such an inspection apparatus (Japanese Patent Application Laid-Open No. H06-018421). As shown in FIG. 10, in this device 11, semiconductors 1, 6 having light emitting elements 2 and light receiving elements 7, respectively, are joined and integrated with a gap corresponding to a flow path 10 being present therebetween. The device 11 measures the concentration of an objective component existing in the flow path 10 based on a change in a light propagating from the light emitting elements 2.

Moreover, as a constitutional example of an optically gated terahertz transmitter/receiver for transmitting/receiving a terahertz wave, an antenna structure formed on a semiconductor substrate, as shown in FIGS. 11A and 11B, is used in many cases. When transmitting a terahertz wave, as shown in FIG. 11A, a gap between dipole antennas of a PC antenna is irradiated with a laser light under application of a DC bias voltage between transmission lines. On the other hand, when receiving a terahertz wave, as shown in FIG. 11B, in a state in which a gap between dipole antennas of a PC antenna is irradiated with a laser light, an electric current flow between transmission lines generated by incidence of a terahertz wave on a substrate is measured by an ammeter.

Water has a strong absorption spectrum for the terahertz wave. Accordingly, as with Japanese Patent Application Laid-Open No. H08-320254 above, when a terahertz wave is allowed to propagate through the atmosphere, the electromagnetic wave will be remarkably attenuated by the influence of water existing in the atmosphere. To reduce the influence of the atmosphere on an electromagnetic wave, there is needed, for example, a means of adjusting the environment at least with respect to a region surrounding the propagation path of the electromagnetic wave. In this case, there is a problem that the provision of the means of adjusting the environment makes the apparatus large-sized. Also, there is another problem that the characteristics of substances present in the atmosphere are liable to be simultaneously detected to thereby sense unwanted signal components, thus increasing noise components.

DISCLOSURE OF THE INVENTION

In view of the above problems, an object of the present invention is to provide an inspection apparatus having reduced electromagnetic wave attenuation.

Accordingly, the present invention provides an inspection apparatus comprising:

a substrate having therein a structure for holding an inspected object;

an electromagnetic wave transmitting portion having an antenna structure for irradiating the inspected object with an electromagnetic wave; and an electromagnetic wave receiving portion having an antenna structure for receiving the electromagnetic wave, wherein the electromagnetic wave transmitting portion and the electromagnetic wave receiving portion are disposed in contact with the substrate.

In the present invention, it is preferred that the inspection apparatus is configured such that an electromagnetic wave generated in the electromagnetic wave transmitting portion propagates through the substrate, and the electromagnetic wave receiving portion receives an electromagnetic wave which is changed when the inspected object is disposed in an electromagnetic wave propagation path.

According to the present invention, there is obtained the effect that the electromagnetic wave attenuation resulting from an environment surrounding the inspection apparatus can be suppressed. Further, because a structure is adopted in which an unwanted substance is readily prevented from being contaminated into an electromagnetic wave propagation path, there is also obtained the effect that the detection sensitivity improves.

BEST MODE FOR CARRYING OUT THE INVENTION

Figure 1A:
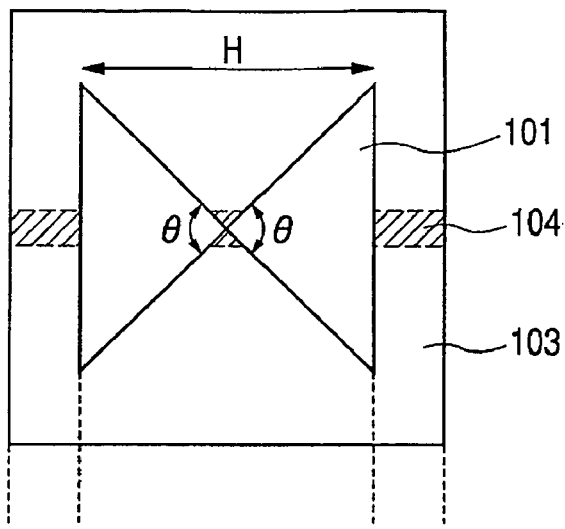
FIGS. 1A, 1B and 1C are a plan view, a side view and a rear view for explaining an inspection apparatus according to an embodiment and Example 1 of the present invention, respectively.

Specific configurations for carrying out the present invention will be described with reference to the drawings. Incidentally, like reference numerals will refer to like elements in the respective figures.

Figure 1B:
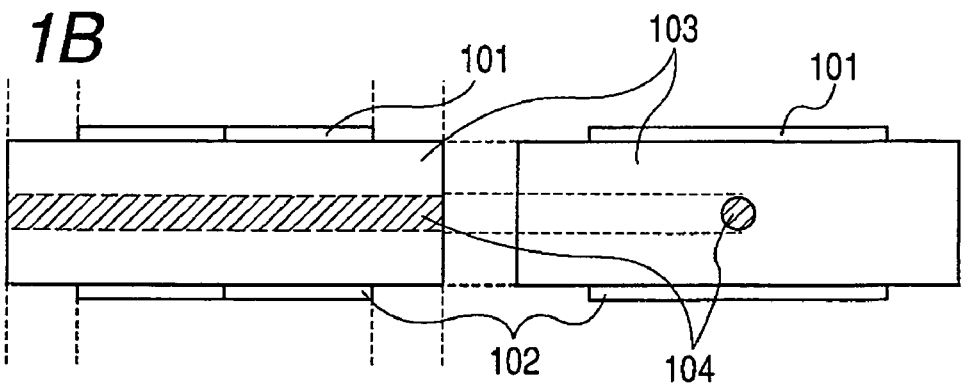
Figure 1C:
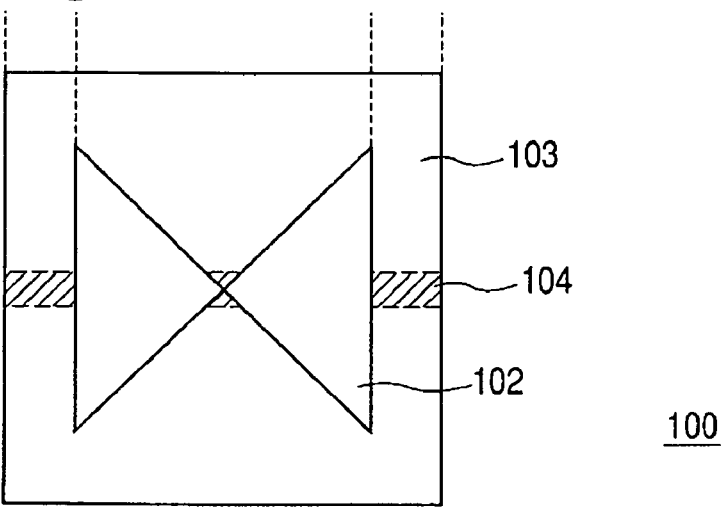

FIGS. 1A, 1B and 1C are a plan view, a side view and a rear view for showing a schematic configuration of an inspection apparatus according to one embodiment of the present invention, respectively. As shown in FIGS. 1A, 1B and 1C, the inspection apparatus 100 according to the present embodiment has a configuration in which a THz wave transmitting portion 101 and a THz wave receiving portion 102 are disposed in contact with the surfaces of an inspected object holding portion 103 (hereinafter sometimes referred to as "substrate") having therein a structure for holding an inspected object 104. The inspected object 104 is held within the structure which the inspected object holding portion 103 has inside thereof. In the present embodiment, as shown in FIGS. 1A, 1B and 1C, the interior structure of the inspected object holding portion 103 for holding the inspected object 104 has a cylindrical shape, but is not limited to this shape. Any structure capable of holding the inspected object 104 within the inspected object holding portion 103 can be used. Further, it is preferable that the inspected object holding portion 103 has a structure which allows the inspected object 104 to be inserted from the outside.

Figure 6:
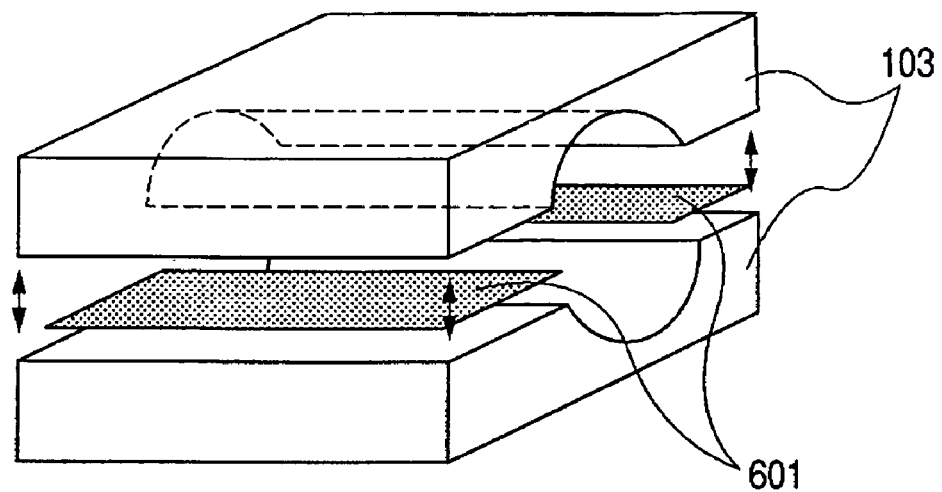
FIG. 6 is a schematic view for explaining an example of the production steps of an inspection apparatus according to the present invention.

The inspected object holding portion 103 is fabricated by using a processing technique applied to an ordinary MEMS (Micro Electro Mechanical Systems) fabrication technique or the like. For example, as shown in FIG. 6, a technique is employed in which recess portions are formed in part of two substrates for constituting an inspected object holding portion 103, and thereafter the two substrates are bonded and integrated by use of a resin adhesive layer 601 with the recess portions facing each other. However, it should be noted that the technique of bonding the substrates is not limited to the one using the resin adhesive 601, and any technique or system using a substance capable of bonding and integrating the substrates can be used. Further, the technique is not limited to such bonding, and any technique can be employed which allows a structure for holding an inspected object 104 to be formed in the interior of the inspected object holding portion 103.

The THz wave transmitting portion 101 and THz wave receiving portion 102 each have an antenna structure comprised of a conductor. For example, in the present embodiment, as shown in FIGS. 1A, 1B and 1C, a structure is employed in which two triangular conductors are opposed to each other with the vertexes facing each other with a minute gap (not shown) therebetween. This antenna configuration is called a bow-tie antenna, and known as a wide-band antenna which functions as an antenna with respect to an electromagnetic wave signal of a higher frequency than a wavelength calculated from the antenna height H (corresponding to a distance between the bases of the triangles). Further, it is also known that the antenna impedance varies depending on the center angle θ of the antenna.

Figure 11A:
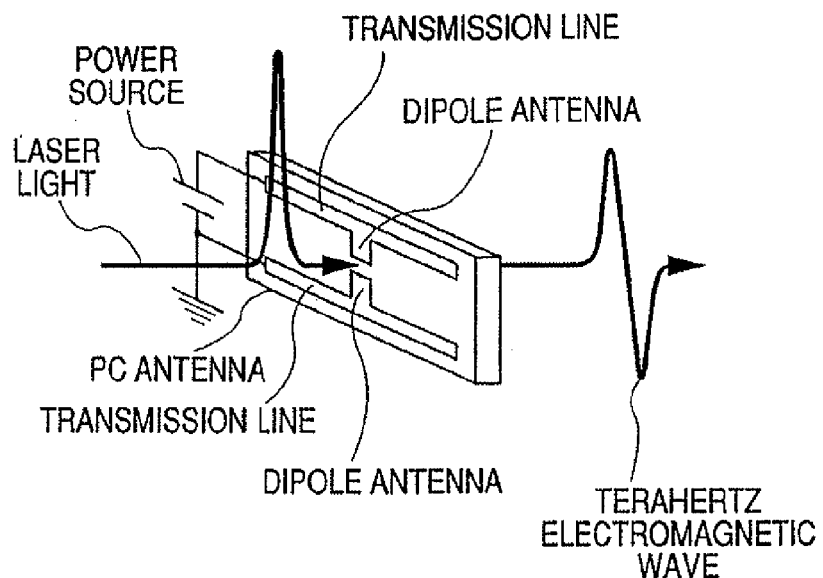
FIG. 11A is a schematic diagram for explaining a method of transmitting a terahertz wave using a photoconductive antenna (PC antenna)
Figure 11B:
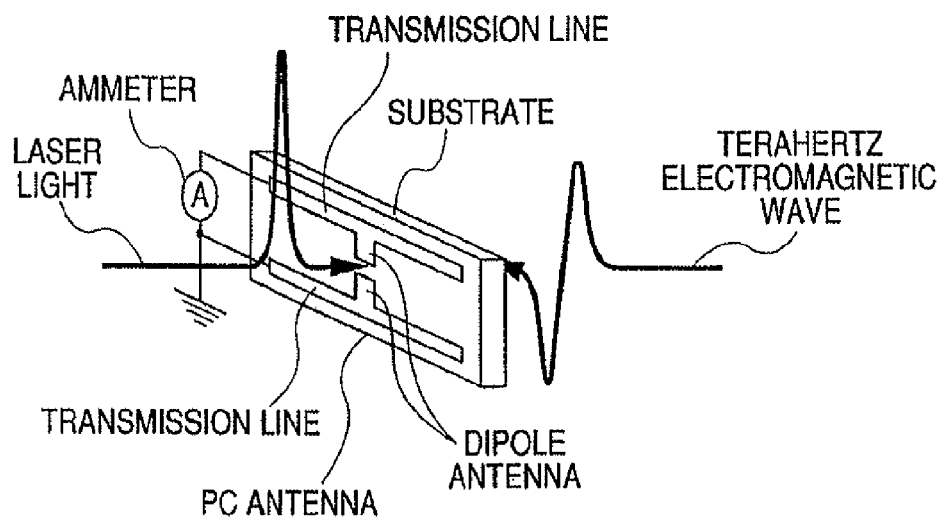
FIG. 11B is a schematic diagram for explaining a method of receiving a terahertz wave using a PC antenna.

Of course, the antenna structure according to the present embodiment is not limited thereto, and appropriately selected depending on required characteristics such as band, directivity and impedance matching. In the present embodiment, as described above, the center portion of the antenna structure has a minute gap, and as described in BACKGROUND ART above with reference to FIGS. 11A and 11B, the gap is optically gated to generate and detect an electromagnetic wave (when generating it, a bias voltage is applied to the gap, and when detecting it, a laser light is irradiated to the gap). However, it should be noted that such structure is also appropriately selected according to the technique of generating/detecting a terahertz wave. Such structure is fabricated by use of an ordinary print technique. However, the technique is not limited thereto and it is only necessary to be capable of forming a desired conductor pattern.

In the THz wave transmitting portion 101, the gap of the antenna structure is optically gated to generate an electromagnetic wave. For example, it is known that when a GaAs substrate having low-temperature-grown GaAs (LT-GaAs) epitaxially grown on a surface thereof is used as the inspected object holding portion 103, the electromagnetic wave band exists in the terahertz wave region. However, the material used for the inspected object holding portion 103 is not limited thereto. According to the desired electromagnetic wave characteristics, the structure and processing conditions of the inspected object holding portion 103, and the like, appropriate selection is made from, for example, a substrate having a gain structure capable of achieving an electromagnetic wave gain, a substrate obtained by transferring a LT-GaAs epitaxially grown thin film on a desired substrate such as a Si substrate, and the like.

As described above, electromagnetic waves are liable to be confined within the substrate due to a difference in refractive index at an interface with the atmosphere or the like, so that most of the generated terahertz waves propagate within the inspected object holding portion 103. When an inspected object 104 exists in a terahertz wave propagation path, and when a frequency absorption spectrum specific to the inspected object 104 exists within the terahertz wave region, a part of frequency components of the terahertz wave propagating within the inspected object holding portion 103 is absorbed, so that the propagation state of the terahertz wave will change. The change includes changes in parameters such as phase, intensity, and waveform of the electromagnetic wave. It is preferable that the absorption spectrum of the inspected object 104 exists within the terahertz wave region. However, even when the absorption spectrum of the inspected object 104 does not exist within the terahertz wave region, the propagation state of the terahertz wave propagating within the inspected object holding portion 103 will change due to physical characteristics (for example, refractive index of loss) of the inspected object 104. Such change is detected by the THz wave receiving portion 102.

In the THz wave receiving portion 102, as described above, by optically gating the gap of the antenna structure constituting the portion, a terahertz wave propagating within the inspected object holding portion 103 is detected. In the present embodiment, to generate/detect an electromagnetic wave in the terahertz wave region, the optical gating system described above is used. However, the technique is not limited to such a system, and it is only necessary to be capable of generating/detecting an electromagnetic wave in the terahertz wave region (see Examples described below).

Further, as shown in FIGS. 1A to 1C, in the present embodiment, the THz wave transmitting portion 101 and the THz wave receiving portion 102 are disposed face each other with the inspected object holding portion 103 (i.e., substrate) therebetween. When the THz wave transmitting portion 101 and the THz wave receiving portion 102 are disposed along a direction perpendicular to the thickness direction of the substrate (i.e., parallel to the principal surface of the substrate) in this way, the propagation distance of the terahertz wave can easily be varied by changing the thickness of substrate, which is preferable. However, the configuration is not limited thereto. For example, the two portions may be disposed on the same surface of the inspected object holding portion 103. Further, when disposed facing each other, the THz wave transmitting portion 101 and THz wave receiving portion 102 may be offset with respect to each other. It is only necessary that the two portions are disposed such that a terahertz wave generated in the THz wave transmitting portion 101 and propagating through the inspected object holding portion 103 via an inspected object 104 can be received by the THz wave receiving portion 102.

There will be described below an embodiment adapted to an inspection apparatus which, by use of the aforementioned inspection apparatus 100, practically acquires physical property information of an inspected object 104 and performs analysis, identification or the like of the inspected object 104.

Figure 2:
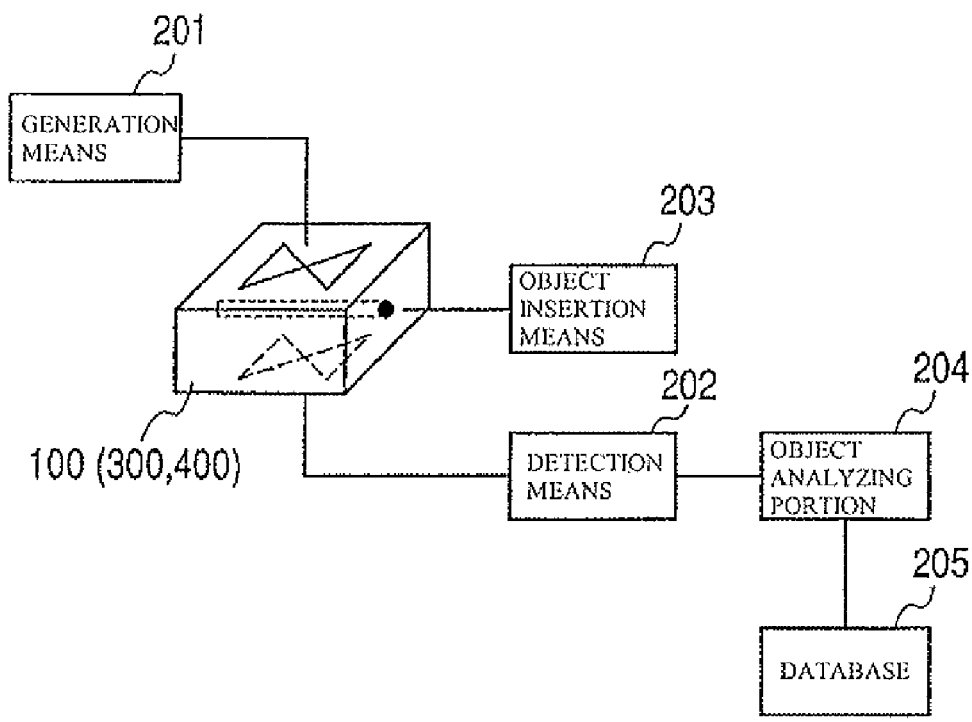
FIG. 2 is a diagram showing an exemplary configuration of an inspection apparatus according to the present invention.

As schematically shown in FIG. 2, in the inspection apparatus according to the present embodiment, generation means 201 for generating a electromagnetic wave and detection means 202 for detecting an electromagnetic wave are additionally connected to the inspection apparatus 100. As the generation means 201 in the present embodiment, there may be used any device or apparatus of any configuration as long as it allows the THz wave transmitting portion 101 constituting the inspection apparatus 100 to generate a terahertz wave. For example, when the THz wave transmitting portion 101 has an antenna conductor structure having a gap as described above, the generation means 201 corresponds to a light source and an optical system for gating the gap, and a bias applying power source. Similarly, as the detection means 202 in the present embodiment, there may be used any device or apparatus of any configuration as long as it can detect a terahertz wave received by the THz wave receiving portion 102 constituting the inspection apparatus 100. For example, when the THz wave receiving portion 102 has an antenna conductor structure having a gap as described above, the detection means 202 corresponds to a light source and an optical system for gating the gap, and a current detection means.

Specifically, as the light source of the detection means 202, a femtosecond laser light source is used. Further, the current detection means is constituted of a current input preamplifier and an information processing device for forming a waveform of a terahertz wave. When the gap between antennas is gated by a laser generated by the light source, the current input preamplifier detects a current corresponding to the electric field strength of a terahertz wave incident on the antenna. However, this current signal has a current value at the moment when gated. Therefore, an optical delay system, for example, is used to vary the timing of laser incidence on the antenna gap and the waveform is observed. In the information processing device, current values at respective laser timing are plotted in a time domain to form a terahertz wave. That is, this corresponds to sampling/detection of a terahertz wave with a short-pulse laser. A spectroscope using this technique is generally called a terahertz-wave time-domain spectroscope (THz-TDS). In the detection means 202, a terahertz wave is detected by use of such technique.

Moreover, in the inspection apparatus according to the present embodiment, to the inspection apparatus 100, there is further provided a configuration which uses an inspected object insertion means 203 for inserting an inspected object 104 from the outside into the inspected object holding portion 103 of the inspection apparatus 100. As the inspected object insertion means 203, any means of any configuration can be employed as long as it can achieve the object of inserting into the inspected object holding portion 103 an inspected object used for analysis. Examples of such means include a technique of using an actuator to perform insertion, a technique of using inkjet technology to perform insertion by jetting, a technique of using a needle to perform insertion, and a technique of using a physical phenomenon at an interface such as a capillary phenomenon to perform insertion.

The detection means 202 acquires from the THz wave receiving portion 102 the waveform of a terahertz wave which has propagated through the inspected object holding portion 103 and whose propagation state has been varied by the presence of the inspected object 104. An inspected object analyzing portion 204 compares the information on the terahertz wave acquired by the detection means 202 with the information on a substance preliminarily stored in a database 205 to perform analysis, identification or the like of the inspected object. For example, the inspected object analyzing portion 204 can compare the frequency spectrum of the terahertz wave acquired by the detection means 202 with the frequency spectrum of the substance stored in the database 205 to identify the constitutional components of the inspected object. However, the information to be compared is not limited thereto, and an information to intensity variation or phase variation can also be used. Further, it is preferable that data of as many substances as possible are stored in the database 205.

In the present embodiment, attention is paid, particularly, to a terahertz wave. However, it will easily be appreciated that the inspection apparatus according to the present invention can also be applied to electromagnetic wave outside the terahertz frequency region.

The inspection apparatus according to the present embodiment, because of having the configuration and operation as described above, can perform analysis, identification or the like of an inspected object 104 without causing a terahertz wave for detection purpose to propagate through an environment surrounding the inspection apparatus. Accordingly, attenuation of the terahertz wave can be suppressed, so that there is obtained the effect such that the signal strength is increased to facilitate the detection operation.

Moreover, because an unwanted substance can readily be prevented from being contaminated into a terahertz wave propagation path, there is also obtained the effect that noise components (in the case of the present embodiment, a change in the propagation state of the electromagnetic wave caused by an unwanted substance) are suppressed to improve the detection sensitivity. Moreover, it is also possible to make the inspection apparatus small-sized.

EXAMPLES

More specific examples will be described below with reference to the drawings.

Example 1

FIGS. 1A, 1B and 1C show one example of an inspection apparatus according to the present invention. Incidentally, it is noted that, in the present example, the operation verification of an inspection apparatus is performed by calculation using an electromagnetic field simulator.

As shown in FIGS. 1A, 1B and 1C, the inspection apparatus 100 of the present example is constituted by a THz wave transmitting portion 101, a THz wave receiving portion 102, and an inspected object holding portion 103. The THz transmitting portion 101 and THz receiving portion 102 each have a bow-tie type antenna structure in which conductors each having an isosceles triangle shape with a vertical angle θ=90° are disposed in opposition to each other. The antenna structure of the present example has an antenna height H of 1 mm. In the present example, the antenna structure has a gap (not clearly shown in the figures) of 5 μm at the center thereof (i.e., between the vertexes of the two triangular conductors). In the present example, the antenna structures are formed by an evaporation process using AuGe/Ni/Au so as to face each other with the inspected object holding portion 103 therebetween, as shown in FIGS. 1A, 1B and 1C.

The inspected object holding portion 103 is a substrate for holding an inspected object 104 in a space provided therein such that the inspected object 104 fills the space so as to leave substantially no empty space. As shown in FIG. 6, the inspected object holding portion 103 is obtained by forming, by use of the processing technique such as described above, a recess portion having a semi-cylindrical shape of 60 μm in radius in a surface of a GsAs substrate of 100 μm in thickness having an LT-GaAs epitaxially grown layer of 1.5 μm in thickness thereon, and then bonding and integrating the thus processed two substrates by use of a resin adhesive 601. As a result, a cylindrical space of 60 μm in radius is fabricated within the thus bonded GaAs substrate of 200 μm in thickness.

In the present example, as the THz wave transmitting portion 101 and the THz wave receiving portion 102, the antenna structures having the gap are used. Accordingly, as described above, by optically gating the gap portion, an electromagnetic wave can be generated/detected. At this time, the electromagnetic wave will be a terahertz wave. In order to optically gate the gap portion of the antenna structure in this manner, a femtosecond laser is used as the generation means 201 (see FIG. 2) of the inspection apparatus, and the detection means 202 (see FIG. 2) of the inspection apparatus is constituted of an optical device having an optical delay system in which an femtosecond laser light is time delayed.

In the inspection apparatus 100 constituted as described above, an inspected object 104 is inserted in the cylindrical space. Thus, the inspection apparatus shown in FIG. 2 can detect a terahertz wave whose propagation state has been varied by the presence of the inspected object 104, and in the inspected object analyzing portion 204, the information stored in the database 205 is referred to, whereby analysis, identification or the like of the inspected object 104 becomes possible.

Figure 7:
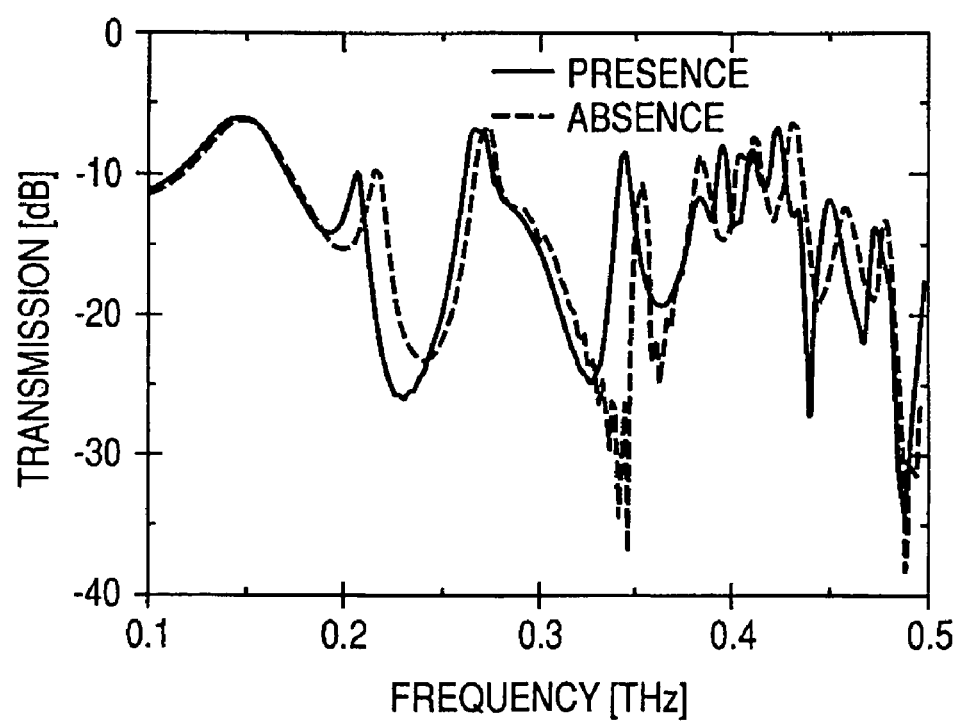
FIG. 7 is a graphical representation for explaining the operation of the inspection apparatus according to Example 1 of the present invention.

FIG. 7 is a graphical representation obtained by calculating the state of propagation of a terahertz wave from the THz wave transmitting portion 101 to the THz wave receiving portion 102 when DNA (dielectric constant: 4.0; dielectric loss tangent (tan δ): 0.01) is used as the inspected object 104. Referring to FIG. 7, the solid line indicates the propagation state of terahertz wave when the inspected object 104 is present, and the broken line indicates the propagation state of terahertz wave when the inspected object 104 is absent. As is clearly seen from FIG. 7, the frequency characteristics of the terahertz wave are shifted to the lower frequency side by the presence of the inspected object 104. It can also be seen that the intensity (transmittance) also varies depending on the frequency. In this calculation, as the physical characteristics of the inspected object 104, only the dielectric constant and dielectric loss tangent are considered. However, when an effect of absorption of an electromagnetic wave depending on frequency spectrum specific to this inspected object 104 is considered, it can be expected that a more noticeable change in the frequency spectrum occurs.

In the present example, the THz wave transmitting portion 101 and the THz wave receiving portion 102 are disposed to face each other via the inspected object holding portion 103. However, the present invention is not limited to such arrangement. For example, as described above, when the effect of terahertz wave confinement in the inspected object holding portion 103 is utilized, even when the THz wave transmitting portion 101 and the THz wave receiving portion 102 are fabricated on the same surface of the inspected object holding portion 103, a terahertz wave can be detected in the THz wave receiving portion 102. Further, when such terahertz wave confinement effect is applied, an inspected object 104 contained in the inspected object holding portion 103 does not always have to be disposed just under the THz wave transmitting portion 101, and the THz wave transmitting portion 101 and the THz wave receiving portion 102 can be disposed at any positions. Moreover, when the apparatus is controlled such that the operations of the generation means 201 and detection means 202 constituting the inspection apparatus are alternately performed, the generation/detection operation can be performed by either one of the THz wave transmitting portion 101 and the THz wave receiving portion 102.

Also, in the present example, as the technique for generating/detecting a terahertz wave, a technique is described in which a femtosecond laser is used to perform optical gating. However, the present invention is not limited to this technique. For example, the following configuration can be employed.

Figure 4:
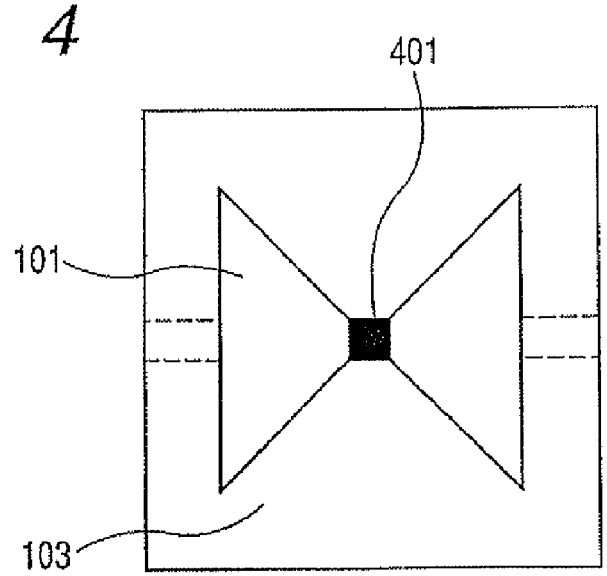
FIG. 4 is a plan view for explaining a modified example of the inspection apparatus according to the example of the present invention.

As shown in FIG. 4, a configuration may be employed which a negative resistance element 401 is provided at the center portion of the THz wave transmitting portion 101 and the THz wave receiving portion 102. The negative resistance element 401 is a semiconductor device, as typified by a resonant tunneling diode (RTD) or a Gunn diode, capable of achieving an electromagnetic wave gain. In such a configuration, a bias voltage can be applied from outside to the negative resistance element 401 to generate a terahertz wave in the THz wave transmitting portion 101 and to detect the terahertz wave in the THz wave receiving portion 102. When such an inspection apparatus 400 is used, the generation means 201 for generating a terahertz wave and the detection means 202 for detecting a terahertz wave of the inspection apparatus are each constituted by a bias circuit.

Figure 5:
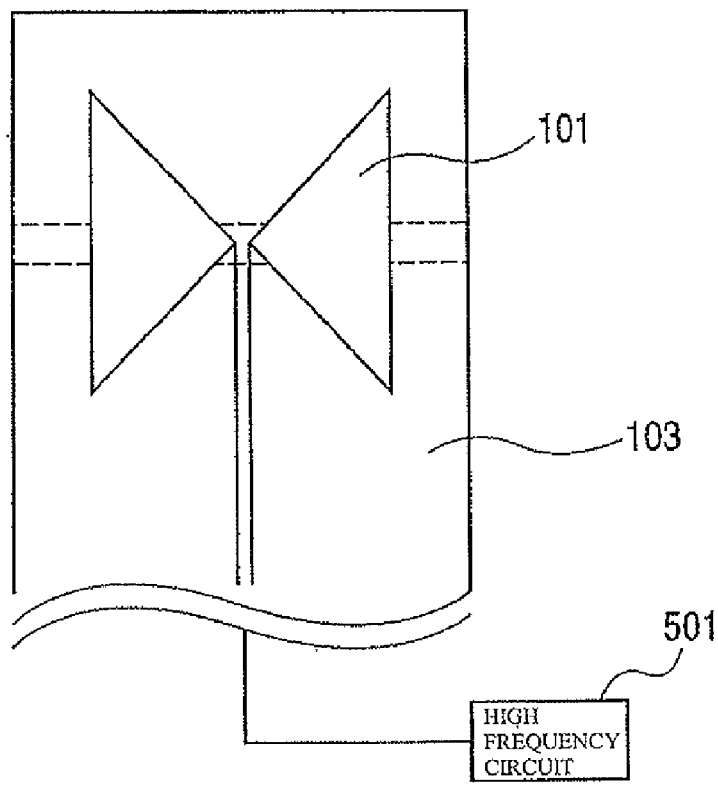
FIG. 5 is a plan view for explaining a modified example of the inspection apparatus according to the example of the present invention.

In addition, in the aforementioned example, the THz wave transmitting portion 101 and the THz wave receiving portion 102 are constituted so as to function also as elements for generating/detecting a terahertz wave. However, as shown in FIG. 5, a configuration may be employed in which a high frequency circuit 501 having a function of generating or detecting a terahertz wave is connected to the THz wave transmitting portion 101 or the THz wave receiving portion 102 via a waveguide.

As described above, in the inspection apparatus of the present example, analysis, identification, or the like of an inspected object can be performed without causing a terahertz wave to propagate through the environment surrounding the inspection apparatus. Thus, the attenuation of a terahertz wave can be suppressed, so that the signal intensity increases to thereby facilitate the detection operation. Further, an unwanted substance is readily prevented from being contaminated into the terahertz wave propagation path, so that noise components (in the case of the present example, a change in the propagation state of the electromagnetic wave caused by an unwanted substance) are suppressed to thereby improve the detection sensitivity. Moreover, by utilizing the terahertz wave confinement effect, there is obtained the effect that the degree of freedom in layout of the elements used to generate/detect a terahertz wave is increased. Furthermore, by performing the generation/detection operation using a single antenna structure, there is obtained the effect that the inspection apparatus production steps can be decreased to thereby reduce the production cost. In addition, by incorporating a semiconductor device having an electromagnetic wave gain into the inspection apparatus, optical components of the inspection apparatus used for generating/detecting a terahertz wave can be remarkably decreased, so that there is obtained the effect that the size of the apparatus can easily be reduced.

Example 2

Figure 3:
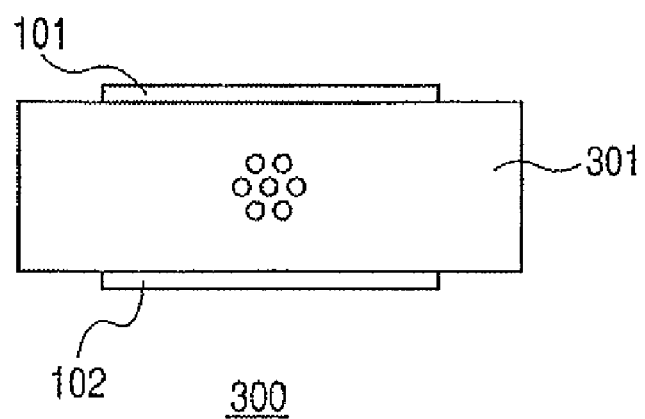
FIG. 3 is a cross-sectional view for explaining an inspection apparatus according to Example 2 of the present invention.

FIG. 3 shows a second example of the inspection apparatus according to the present invention. Incidentally, it is noted that, also in the present example, the operation verification of an inspection apparatus is performed by calculation using an electromagnetic field simulator. As shown in FIG. 3, the inspection apparatus 300 is constituted by a THz wave transmitting portion 101, a THz wave receiving portion 102, and an inspected object holding portion 301. Referring to FIG. 3, a major difference between the inspection apparatus of Example 1 described above and the inspection apparatus 300 of the present example lies in that a plurality of structures, formed in the inspected object holding portion 301, for holding an inspected object 104 (not shown) are periodically disposed to form a resonant structure.

As with Example 1 above, the THz transmitting portion 101 and THz receiving portion 102 each have a bow-tie type antenna structure in which conductors each having an isosceles triangle shape with a vertical angle θ=90° are disposed in opposition to each other. Further, the antenna structure of the present example has an antenna height H of 1 mm. Also in the present example, the antenna structure has a gap (not clearly shown in the figures) of 5 μm at the center thereof (i.e., between the vertexes of the two triangular conductors). Moreover, the antenna structures are formed by an evaporation process using AuGe/Ni/Au so as to face each other with the inspected object holding portion 301 having the resonant structure within a GaAs substrate of 200 μm in thickness having an LT-GaAs epitaxially grown layer of 1.5 μm in thickness on the surface thereof therebetween, as with Example 1.

In the present example, the structure of the resonant portion of the inspected object holding portion 301 is such that cylindrical spaces of 9 μm in radius are disposed at intervals of 40 μm in a triangular lattice arrangement. Such a structure can be well fabricated by the current MEMS technique. By holding an inspected object 104 by means of such a resonant structure, a terahertz wave propagating through the inspected object holding portion 301 is strongly localized in a portion in which the inspected object 104 is present, so that the interaction with the inspected object 104 is increased. Consequently, the change, caused by the inspected object 104, in the propagation state of a terahertz wave propagating within the inspected object holding portion 103 can also be made more noticeable.

Also in the present example, because the antenna structures having the gap are used as the THz wave transmitting portion 101 and THz wave receiving portion 102, when the gap portion is optically gated, an electromagnetic wave can be generated/detected. At this time, the electromagnetic wave will be a terahertz wave. In this manner, similarly to Example 1 described above, the gap portion of the antenna structure is optically gated.

With the inspection apparatus 300 constituted as described above, an inspected object 104 is inserted into the cylindrical spaces as periodically disposed. Thereby, the inspection apparatus shown in FIG. 2 can detect a terahertz wave whose propagation state has been varied by the presence of the inspected object 104, so that analysis, identification, or the like of the inspected object 104 can be performed in the inspected object analyzing portion 204 by referring to the information stored in the database 205.

Figure 8:
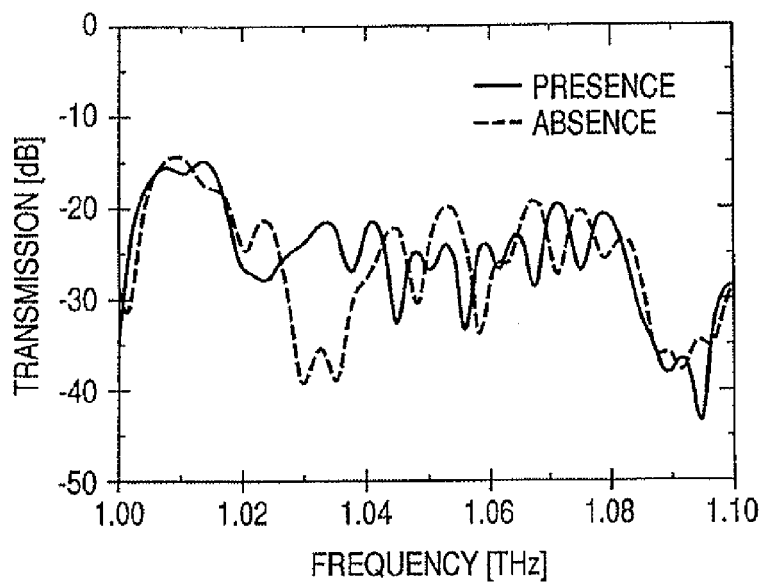
FIG. 8 is a graphical representation for explaining the operation of the inspection apparatus according to Example 2 of the present invention.
Figure 9:
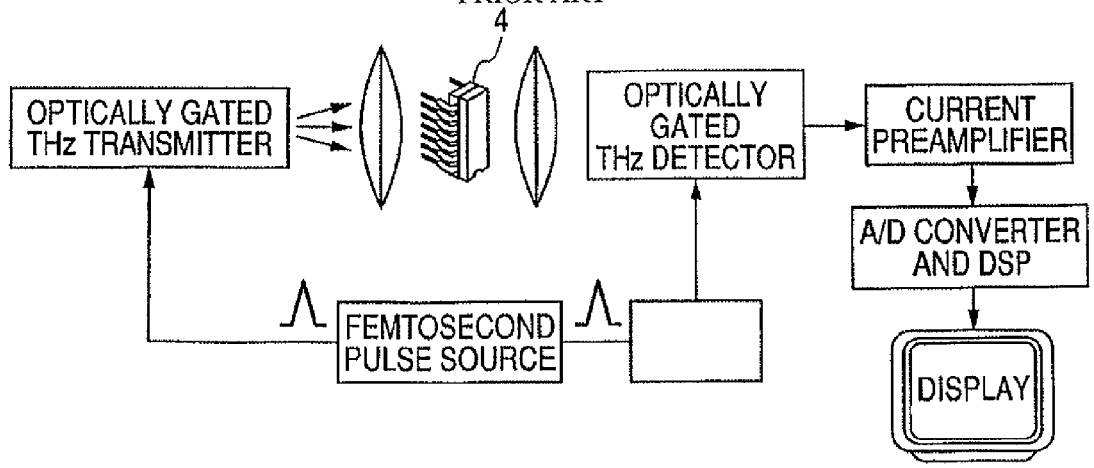
FIG. 9 is a view for explaining the background art of an inspection apparatus using a terahertz wave.
Figure 10:
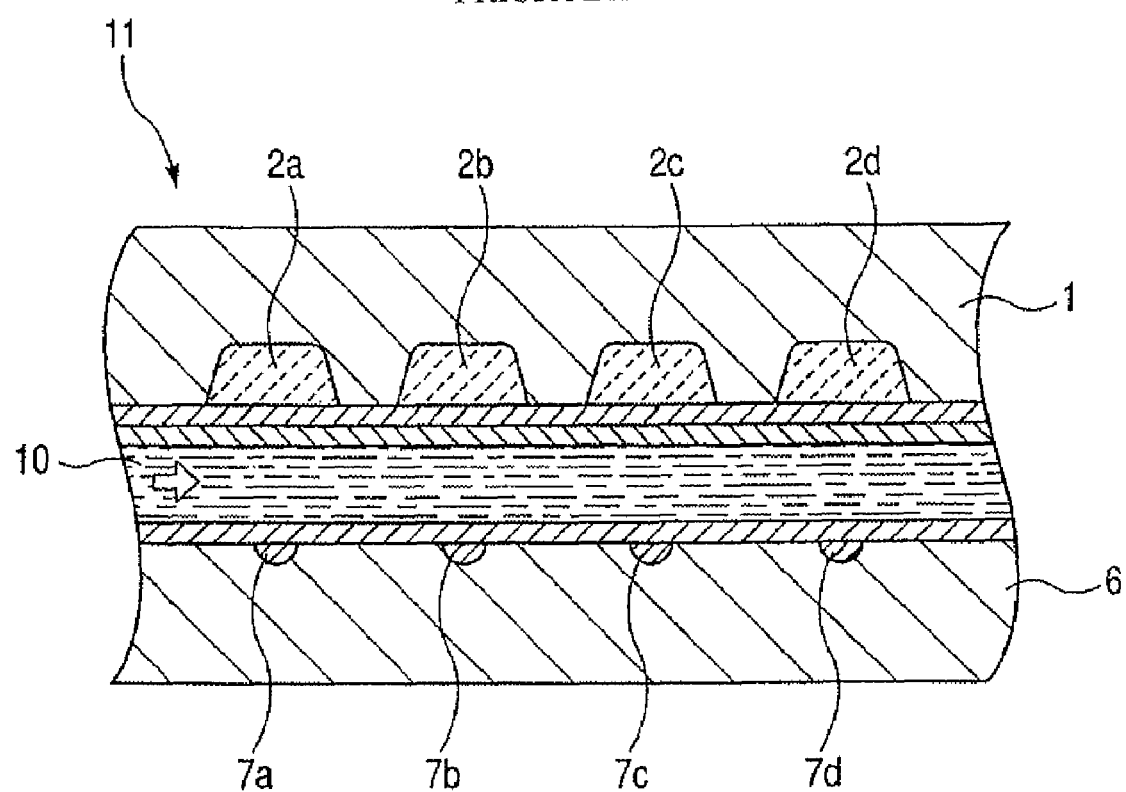
FIG. 10 is a cross-sectional view for explaining the background art of an inspection apparatus using light.

FIG. 8 is a graphical representation obtained by calculating the state of propagation of a terahertz wave from the THz wave transmitting portion 101 to the THz wave receiving portion 102 when DNA (dielectric constant: 4.0; dielectric loss tangent (tan δ): 0.01) is used as the inspected object 104. Referring to FIG. 8, the solid line indicates the propagation state of terahertz wave when the inspected object 104 is present, and the broken line indicates the propagation state of terahertz wave when the inspected object 104 is absent. As is clearly seen from FIG. 8, the frequency characteristics of the terahertz wave are shifted to the lower frequency side by the presence of the inspected object 104. Particularly, in the present example, the configuration of the resonant structure is designed such that the resonant frequency is at about 1 THz. Referring to FIG. 8, it can be seen that the intensity of frequency components in the vicinity of 1.03 THz remarkably changes due to the presence of the inspected object 104. In this calculation, as the physical characteristics of the inspected object 104, only the dielectric constant and dielectric loss tangent are considered. However, when an effect of absorption of an electromagnetic wave depending on frequency spectrum specific to this inspected object 104 is considered, it can be expected that a more noticeable change in the frequency spectrum occurs.

In the present embodiment, as the structure of the inspected object holding portion 103, there is used a resonant structure in which cylindrical spaces are disposed in a triangular lattice arrangement. However, the present invention is not limited to this structure. For example, in place of the cylindrical spaces, there may be used spaces of another shape such as a square pole shape or the like. Further, the manner of disposition is not limited to a triangular lattice arrangement, and a square lattice arrangement may also be employed. In short, any configuration can be employed as long as a resonant action can be achieved by periodical arrangement of the spaces in the inspected object holding portion 301. Moreover, in a part of the periodical arrangement of spaces, there may exist a structure which disturbs the periodicity. This is obtained by, for example, disposing within a photonic band gap structure, a periodicity-disturbing structure which allows only an electromagnetic wave of a particular frequency to pass therethrough.

Thereby, the influence of the inspected object 104 on the electromagnetic wave of the particular frequency can be measured more noticeably.

In addition, also in the present example, as the technique of generating/detecting a terahertz wave, there is described a configuration in which optical gating is performed by use of a femtosecond laser. However, the present invention is not limited to this technique. For example, the aforementioned configuration shown in FIG. 4 can also be employed. Further, also in Example 2, the THz wave transmitting portion 101 and the THz wave receiving portion 102 are constructed so as to function also as elements for generating/detecting a terahertz wave. However, they may have a constitution such as shown in FIG. 5 above.

The inspection apparatus of Example 2 as described above has the following advantageous effect in addition to the effects described above for Example 1. By localizing a terahertz wave in a portion in which an inspected object exists, the interaction between the terahertz wave and the inspected object can be intensified, thus improving the detection sensitivity and facilitating analysis or identification with a higher accuracy.

This application claims priority from Japanese Patent Application No. 2005-087326 filed on Mar. 24, 2005, which is hereby incorporated by reference herein.

The invention claimed is:

1. An inspection apparatus comprising:
    a substrate having integrated therein a structure for holding an inspected object;
    an electromagnetic terahertz wave transmitting portion having an antenna structure for irradiating the inspected object with an electromagnetic terahertz wave; and
    an electromagnetic terahertz wave receiving portion having an antenna structure for receiving the electromagnetic terahertz wave,
    wherein the electromagnetic terahertz wave transmitting portion and the electromagnetic terahertz wave receiving portion are disposed on opposite sides of the substrate facing each other with the substrate therebetween and are in contact with the substrate, and
    the structure for holding the inspected object is between the electromagnetic terahertz wave transmitting portion and the electromagnetic terahertz wave receiving portion.

2. The inspection apparatus according to claim 1, wherein an electromagnetic terahertz wave generated in the electromagnetic terahertz wave transmitting portion propagates through the substrate, and the electromagnetic terahertz wave receiving portion receives an electromagnetic terahertz wave which is changed when the inspected object is disposed in an electromagnetic wave propagation path.

3. The inspection apparatus according to claim 1, wherein the structure for holding the inspected object comprises a plurality of portions for holding the inspected object, periodically disposed to form a resonant structure.

4. The inspection apparatus according to claim 1, wherein at least one of the electromagnetic terahertz wave transmitting portion and the electromagnetic terahertz wave receiving portion comprises a negative resistance element.

5. The inspection apparatus according to claim 1, wherein at least one of the electromagnetic terahertz wave transmitting portion and the electromagnetic terahertz wave receiving portion is connected to a high frequency circuit via a waveguide, for allowing an electromagnetic terahertz wave to propagate therethrough.

6. The inspection apparatus according to claim 1, wherein each of the electromagnetic terahertz wave transmitting portion and the electromagnetic terahertz wave receiving portion has both a function of transmitting an electromagnetic terahertz wave and a function of receiving an electromagnetic terahertz wave.

7. The inspection apparatus according to claim 1, further comprising:
    generation means for allowing the electromagnetic terahertz wave transmitting portion to generate an electromagnetic terahertz wave of a desired frequency band;
    detection means for allowing the electromagnetic terahertz wave receiving portion to detect an electromagnetic terahertz wave propagated through the substrate;
    a database for preliminarily storing physical characteristics of the inspected object; and
    an analyzing portion for correlating an information of an electromagnetic terahertz wave detected by the detection means with an information stored in the database to inspect the inspected object.

8. The inspection apparatus according to claim 7, wherein the generation means is a laser oscillator.

9. The inspection apparatus according to claim 1, wherein the electromagnetic terahertz wave transmitting portion and the electromagnetic terahertz wave receiving portion are formed along a direction perpendicular to a thickness direction of the substrate.

10. The inspection apparatus according to claim 1, wherein the structure extends from one end of the substrate to the other end of the substrate, parallel to the surface of the substrate.

11. The inspection apparatus according to claim 1, further comprising an inspected object insertion means for inserting the inspected object from outside into the structure,
    wherein the inspected object insertion means uses inkjet technology to perform insertion by jetting.

12. An inspection apparatus comprising:
    a substrate having integrated therein a structure for holding an inspected object;
    an electromagnetic terahertz wave transmitting portion having an antenna structure for irradiating the inspected object with an electromagnetic terahertz wave;
    an electromagnetic terahertz wave receiving portion having an antenna structure for receiving the electromagnetic terahertz wave; and
    an inspected object insertion means for inserting the inspected object from outside the structure,
    wherein the electromagnetic terahertz wave transmitting portion and the electromagnetic terahertz wave receiving portion are disposed to face each other with the substrate therebetween, and are in contact with the substrate, and
    the inspected object insertion means uses physical phenomenon at an interface, corresponding to a capillary phenomenon, to perform insertion.

* * * * *